United States Patent [19]
Suzuki et al.

[11] Patent Number: 5,296,111
[45] Date of Patent: Mar. 22, 1994

[54] METHOD OF TREATING PHOTOGRAPHIC PROCESSING WASTES

[75] Inventors: Seiji Suzuki; Kozo Aoki; Hiroshi Ishizuka; Yoshiya Ohara, all of Kanagawa, Japan

[73] Assignee: Fuji Photo Film Co., Ltd., Kanagawa, Japan

[21] Appl. No.: 800,128

[22] Filed: Nov. 29, 1991

[30] Foreign Application Priority Data

Nov. 30, 1990 [JP] Japan .................................. 2-330773
Jan. 28, 1991 [JP] Japan .................................. 3-008608

[51] Int. Cl.$^5$ .......................................... C02F 1/461
[52] U.S. Cl. .................................. 204/130; 204/131; 204/149; 210/610; 210/611; 210/626; 210/748
[58] Field of Search ............... 210/610, 611, 626, 748; 204/130, 131, 149

[56] References Cited

U.S. PATENT DOCUMENTS

| | | | |
|---|---|---|---|
| 4,135,976 | 1/1979 | Kitajima | 423/42 |
| 4,271,013 | 6/1981 | Bhattacharyya | 423/356 |
| 4,936,970 | 6/1990 | Weinberg et al. | 204/86 |

*Primary Examiner*—John Niebling
*Assistant Examiner*—Arun S. Phasge
*Attorney, Agent, or Firm*—Sughrue, Mion, Zinn, Macpeak & Seas

[57] ABSTRACT

A method of treating photographic processing wastes is disclosed. The method comprises (1) mixing a silver-recovery system waste and a development system waste from photographic processing to produce a waste mixture, (2) adding to said waste mixture phosphorus as a nutritive substrate in an amount corresponding to at least 2% based on the COD value of the waste mixture, and (3) subjecting the resulting waste mixture to a bio-oxidation treatment using microflora containing sulfur-oxidizing bacteria. The method enables a continuously treatment of high concentration photographic processing wastes with high efficiency over a long period of time.

14 Claims, No Drawings

METHOD OF TREATING PHOTOGRAPHIC PROCESSING WASTES

FIELD OF THE INVENTION

This invention relates to a method of treating photographic processing wastes and, more particularly, to a method of biologically treating photographic processing wastes which contain high concentrations of reducible inorganic sulfur compounds and organic compounds.

It also concerns a method of treating all wastes generated in the course of the photographic processing of silver halide photographic materials, by which loads of pollution by the wastes are reduced.

BACKGROUND OF THE INVENTION

Photographic processing wastes arising from the processing of black-and-white and color photographic materials are usually divided into two classes-those containing silver ion eluted from the photographic materials in an appreciable concentration (silver-present class) and others (silver-absent class), for the purpose of recovery of silver as a valuable metal. Silver is recovered from the silver-containing class by the trade concerned in the disposal of waste liquid. In general the exhausted processing solutions issuing as wastes from the fixation step, and the bleaching and the combined bleaching and fixing steps for processing color photographic materials are grouped into the silver-present class, and the exhausted processing solutions issuing as wastes from the development step are grouped into the silver-absent class. On the other hand, the exhausted processing solutions issuing as wastes from the washing and the stabilization steps are grouped into either silver-present or silver-absent class depending upon their respective silver ion concentrations.

Since photographic processing wastes contain high concentrations of various kinds of inorganic and organic compounds, they cannot be discharged into a sewer or a river as they are. Accordingly, it is necessary for them to be treated to some extent.

Under these circumstances, a number of treatment methods have been studied to make feasible the discharge of such wastes into a sewer or a river. Specifically, known treatment methods for reducing the pollution loads of photographic processing wastes include activated sludge methods [as disclosed, e.g., in JP-B-55-49559 (The term "JP-B" as used herein means an "examined Japanese patent publication"), JP-B-51-12943, JP-A-48-13265 (The term "JP-A" as used herein means an "unexamined published Japanese patent application") and JP-A-50-2353], evaporation methods (as disclosed, e.g., in JP-A-49-89347 and JP-B-56-33996), electrolytic oxidation methods (as disclosed, e.g., in JP-A-48-84462, JP-A-49-119458 and JP-B-53-43478), ion exchange methods (as disclosed, e.g., in JP-B-51-37704, JP-B-53-383 and JP-B-53-43271), reverse osmosis methods (as disclosed, e.g., in JP-A-50-22463) and chemical treatment methods (as disclosed, e.g., in JP-A-53-12152, JP-B-57-37396 and JP-A-61-241746). However, each of these methods have their individual defects as described below.

As for the activated sludge methods, for example, there is difficulty in employing the method disclosed in JP-B-55-49559, wherein the treatment of wastes is carried out under aeration using concentrated oxygen gas ($O_2 > 20.9\%$), to the treatment of wastes with high concentrations corresponding to biological oxygen demand (abbreviated as "BOD" hereinafter) of 3,000 ppm or more, because it is impossible to finish efficiently the decomposition of BOD and the chemical oxygen demand ("COD") components within an appropriate time by subjecting the wastes to subsequent secondary treatment unless the initial BOD of the wastes is controlled to 3,000 ppm at the most. JP-A-50-2353, on the other hand, discloses an oxidation treatment for thiosulfate-containing wastes, wherein the aeration is carried out under the condition that the thiosulfate-containing wastes are mixed with a sulfur oxidizing bacteria containing solution and the pH adjusted to 4-9 and, what is more, the concentration of nitrogenous compounds is controlled to 0.1% or lower, as based on nitrous acid. This treatment, however, has a problem when it is applied to a photographic fixation waste, which is a type of photographic processing waste, because disorganization of the sludge occurs or the treatment efficiency is insufficient. Moreover, although activated sludge methods have low operation cost, they have little effect upon ingredients which are not biodegradable. In particular, activated sludge methods essentially fail in disposal of chelating agents, such as ethylenediamine-tetraacetic acid (EDTA) and the like, present in quantity in photographic processing wastes.

As for chemical treatment methods, the treatment of wastes is known to be carried out by the addition of hydrogen peroxide, persulfates, perhalogenates, halous acids or hypohalous acids. However, all of these methods have very low efficiency in treating photographic processing wastes with high COD values, so that these reagents are always used in large excess resulting in an increase in operational cost.

As for the ion exchange methods and the reverse osmosis methods wherein resins or membranes are used, frequent renewal of the resins or the membranes is required since they become adsorbed or contaminated with ingredients which tend to polymerize, such as developing agents. In these methods also, the operational cost tends to increase. Moreover, in treating concentrated wastes from photographic processing solutions, the resins and the membranes become greatly fatigued, so that it becomes impossible to use them in a short period of time.

As for the electrolytic oxidation methods, they have the following problems in spite of their strong oxidizing power: (1) in the oxidative decomposition of wastes with high COD, an increase in equipment cost and an increase in treatment time occur because a large quantity of electric current is required; (2) pollution of electrodes due to high molecular weight compounds occur because organic compounds present in the wastes, such as a developing agent, tend to polymerize; (3) evolution of poisonous gases such as hydrogen sulfide occurs upon decomposition of lower sulfur compounds such as thiosulfates; (4) insufficient reduction of BOD occurs because the decomposition of organic compounds stops at a level of lower fatty acids with a BOD load, such as acetic acid, propionic acid and the like; and so on.

In order to provide simple and technically easy treatment of photographic processing wastes, the number of steps must be reduced to a minimum and to the addition of special chemicals is to be avoided. In addition, desirably the wastes produced in separate steps should be treated collectively, because photographic processing consists of several steps and the separate treatments of the wastes produced in the respective steps creates difficulties. In particular, collective treatment is desirable for small-scale photofinishing laboratories.

SUMMARY OF THE INVENTION

Therefore, an object of this invention is to provide a method which enables an effective solution to the above-described problems of the prior art.

More specifically, a first object of this invention is to provide a method by which high concentration photographic processing wastes can be continuously treated with high efficiency over a long period of time when the wastes are directly subjected to a biological treatment under simple aeration without any pretreatment being required.

A second object of this invention is to establish an effective and cheap means for rendering photographic processing wastes harmless in order to prevent pollution of the environment, including prevention of both pollution of water and air.

A third object of this invention is to provide an effective means for rendering photographic processing wastes harmless even when the wastes contain ingredients which are non-biodegradable, such as chelating agents including EDTA, as well as ingredients which are biodegradable.

As a result of various studies on the biological treatment of photographic processing wastes, it has been found that the foregoing objects of this invention are achieved effectively by the means described below.

That is, this invention provides a biological treatment which comprises (1) mixing a silver-recovery system waste and a development system waste from photographic processing to produce a waste mixture, (2) adding to the waste mixture phosphorus as a nutritive substrate in an amount corresponding to at least 2% based on the COD value of the waste mixture, and (3) subjecting the resulting waste mixture to a bio-oxidation treatment using microflora containing sulfur-oxidizing bacteria.

Additionally, the COD value as used in this invention signifies the value determined by oxidation using potassium permanganate, namely the value of $COD_{Mn}$. However, the value of $COD_{Mn}$ is replaced by the abbreviation COD in this specification in order to simplify the expression of COD.

DETAILED DESCRIPTION OF THE INVENTION

The treatment process of this invention is described below in detail.

(1) A silver-recovery system waste and a development system waste are mixed, and subjected to the treatment described below. Herein, the mixing ratio of both wastes can be varied. Preferably, the mixing ratio of a silver-recovery system waste to a development system waste is 9:1 to 1:9 by volume, and more preferably 3:7 to 7:3 by volume. When the concentration of inorganic salts in this waste mixture is too high, it is desirable that the waste mixture should be diluted with water by a factor of from 6 to 15 so that the salt concentration is lower than that of seawater (about 3% or less). However, high dilution requires a large-size equipment to achieve a marked increase in land and equipment costs, so that the dilution should be set at the lowest possible level. In this connection, the treatment method of this invention achieves its effect more fully when applied to the high concentration wastes having a COD value of 3,000 to 8,000 ppm, although it can also be applied to wastes with a COD value of 3,000 ppm or less.

(2) Phosphorus is added to the waste mixture to be treated in such an amount corresponding to at least 2% of the COD value of the waste mixture. In addition, it is desirable that an appropriate amount of metallic elements such as calcium, magnesium, etc. should be present. Herein, one or all of the metallic elements may be added in advance to the waste mixture prepared in step (1). On the other hand, it is not necessarily required to add phosphorus before the foregoing waste mixture is passed on to a biological treatment, because phosphorus need only produce its effect during the stage of biological treatment. Consequently, phosphorus may be added to the waste mixture subjected to the biological treatment.

(3) The resulting waste mixture is treated biologically. Methods for a biological treatment which can be used herein include an activated sludge method, a fluid bed method, a contact filtration bed method, a rotating disk contact method, a contact aeration method and other biological contact oxidation methods. The details of these biological treatments are described, e.g., in *Arts of Biological Water-Treatment and Apparatuses Therefor* (compiled by The Society of Chemical Engineers, Japan, published by Baifukan), in *Maintenance Arts of Activated Sludge* (prepared under the supervision of Toshiro Sakurai and Ryuichi Sudo, published by Center for Technical Information of Science), in *Draining Treatment using Microorganism Fixation Process* (prepared under the supervision of Ryuichi Sudo, published by Investigating Committee of Water for Industrial Use), and in *Techniques and Regulations for Antipollution* (prepared under the supervision of the Ministry of International Trade and Industry, published by the Society for the Industrial Antipollution), the disclosure of which is incorporated by reference.

Of the foregoing biological treatments, treatment with activated sludge containing sulfur-oxidizing bacteria is preferred in particular. In a continuous activated sludge treatment system, HRT (hydraulic retention time) is preferably one to two days. Also, the activated sludge treatment of the batch type system can be employed in this invention. Treatment in this system is performed, e.g., as follows: When one day is allotted to one cycle of the steps involved in the treatment, a period of 2 hours is spent in an inflow step, 17 hours in an aeration step in an aeration tank, 2 hours in a sedimentation step, 2 hours in a discharge step, and 1 hour in a waiting step. In both continuous and batch treatments systems, it is desirable to neutralize sulfuric acid, which is produced by the oxidation of lower sulfur compounds such as thiosulfates, thiosulfites, etc. during the treatment, that the interior of the aeration tank should be adjusted to a pH of 5.5–8.5, preferably 5.8–7.5, particularly preferably 6.5–7.0, by the addition of alkalis (e.g., sodium hydroxide, potassium hydroxide, calcium hydroxide, sodium carbonate). Under these conditions, the phosphorus added can perform its function as a nutrient substrate. When the pH of the microflora is in the range of 5.5–8.5, particularly 6.5–7.0 during the biological treatments, sulfur-oxidizing bacteria can fully achieve their activity. Sulfur-oxidizing bacteria are generally contained in activated sludge in an amount of $10^6$ to $10^8$ cells per ml.

Even when the foregoing waste mixture has a high concentration corresponding to a COD value ranging from 3,000–8,000 ppm, satisfactory treatment can be achieved in accordance with the method of this invention.

It is desirable for phosphorus to be present as a nutrient substrate in the foregoing waste mixture in an amount corresponding to from 2% to 5% of the COD value of the waste mixture. The addition of phosphorus may be carried out using various kinds of phosphates, e.g., $KH_2PO_4$, $K_2HPO_4$, $NaH_2PO_4 \cdot 2H_2O$, $Na_2HPO_4$, etc., phosphoric acid or other phosphorus compounds.

The silver-recovery system waste which can be treated in this invention includes the residue obtained after silver is recovered from wastes issuing from the processing baths after removal of silver (desilvering), such as a fixing bath, a bleach-fix bath and a bleaching bath used in a color photographic processing and/or a black-and-white photographic processing, in which a large quantity of reducible inorganic sulfur compounds including ammonium thiosulfate and sodium sulfite are present.

On the other hand, the development system waste refers to wastes issuing from a developing bath, a stabilizing bath, a washing bath and other baths used in a color photographic processing and/or a black-and-white photographic processing, in which organic compounds, such as hydroquinone, color developing agents, etc., are present in high concentrations.

Sulfur-oxidizing bacteria which can be used in this invention are conventional ones, such as those of the genus Thiobacillus including *Thiobacillus thioparus, Thiobacillus neapolitanus, Thiobacillus novellus, Thiobacillus intermedius, Thiobacillus perometabolis*, etc., of the Thiothrix genus, of the Beggiatoa genus, and so on.

In particular, when activated sludge containing a necessary amount of sulfur-oxidizing bacteria such as those of the Thiobacillus genus, of the Thiothrix genus and of the Beggiatoa genus is used as microflora, acclimation of bacteria can be conducted quickly to efficiently oxidize a lower sulfur compound for a short period of time. Therefore, the addition of these sulfur-oxidizing bacteria to activated sludge is preferred.

As a result of the treatment of a large quantity of organic compounds from the development system waste in addition to the above-described inorganic sulfur compounds, it is to be desired that conventional activated sludge also should be used in the treatment of this invention. Under these circumstances, activated sludge containing sulfur-oxidizing bacteria are used in the biological treatment of this invention.

Therefore, conditions under which not only sulfur-oxidizing bacteria but also activated sludge can achieve their respective activities to the full extent are set for the biological treatment of this invention.

JP-A-55-106597 discloses a method in which a waste containing thiosulfate ion, such as that draining from a pyrite mine, is mixed with both solutions in which sulfur-oxidizing bacteria and a nutrient for the sulfur-oxidizing bacteria are present respectively and aerated to effect a treatment with the sulfur-oxidizing bacteria, and JP-A-50-2353 discloses a method in which a thiosulfate-containing waste such as photographic fixation waste is mixed with a thiobacteria-containing solution and subjected to an aeration. However, both of these prior art techniques are directed to the oxidation treatment of thiosulfate ion, and do not deal with a system involving the presence of organic compounds in high concentrations. Thus, no biological treatment which is carried out in the presence of concentrated organic compounds is known.

In this invention, not only is thiosulfate ion and the like but also BOD components such as organic compounds are removed by the biological treatment of the above-described waste mixture using microflora containing sulfur-oxidizing bacteria. In order for the sulfur-oxidizing bacteria to function to their fullest extent in this biological treatment, the microflora is subjected to aeration by using an oxygen-containing gas, such as air.

Photographic processing wastes to which the method of this invention can be applied include all exhausted processing solutions issuing from photographic processing of silver halide photographic materials. The term silver halide photographic material used herein is intended to include both color and black-and-white photographic materials. Examples of color photographic materials, include color papers, color reversal papers, photographic color negative films, color reversal films, motion picture negative and positive films, direct-positive color photographic materials and so on, while examples of a black-and-white photographic material include X-ray films, graphic arts light-sensitive materials, microfilms, photographic black-and-white film, and so on.

The photographic processing wastes issuing from processing baths used in the photographic processing contain, as main components, compounds which make up the processing baths. In addition to these main components, the photographic processing wastes contain reaction products produced during photographic processing, such as oxidation products of developing agents, sulfates, halides and so on, and trace amounts of gelatin and surface active agents eluted from photographic materials.

Processing solutions used in producing photographs include color photographic processing solutions, black-and-white photographic processing solutions, reducing solutions accompanying workings in the graphic arts, cleaning solutions for developing tanks, and so on. Additionally, photographic processing solutions include developing solutions, fixing solutions, bleaching solutions, image stabilizing solutions and so on.

Usually exhausted processing solutions issuing as wastes from the above processing steps are usually divided into two classes-those containing silver ion eluted from photographic materials in an appreciable concentration (silver-present class) and others (silver-absent class), for the purpose of recovery of silver as a valuable metal, and subjected to recovery treatments. In general, exhausted processing solutions issuing from the fixation step in black-and-white photographic processing and those issuing from the bleaching, the fixation and the bleach-fix steps in color photographic processing are grouped into the silver-present class, while exhausted processing solutions issuing from the development step in both color photographic processing and black-and-white photographic processing are grouped into the silver-absent class. Additionally, the exhausted processing solutions issuing from the washing and the stabilization steps in both color photographic processing and black-and-white photographic processing are grouped into either silver-present or silver-absent class depending upon the silver ion concentrations. In this invention, the residue obtained after silver is recovered from the wastes of silver-present class is considered silver-recovery system waste, while the wastes of silver-absent class are considered development system waste. Accordingly, the development system waste to which this invention is applicable contains as main constituents compounds present in exhausted developers.

Usually a color developer contains an aromatic primary amine color developing agent as a main component. Compounds chiefly used as the color developing agent are p-phenylenediamine derivatives, with typical examples including N,N-diethyl-p-phenylenediamine,2-amino-5-diethylaminotoluene, 2-methyl-4-[N-ethyl-N-($\beta$-hydroxyethyl)amino]aniline and N-ethyl-N-($\beta$-methanesulfonoamidoethyl)-3-methyl-4-aminoaniline. These p-phenylenediamine derivatives may be present in the form of the sulfate, hydrochloride, sulfite, p-toluenesulfonate or other salts. The amount of aromatic primary amine developing agent ranges from about 0.5 g to about 10 g per liter of developer.

On the other hand, a black-and-white developer contains 1-phenyl-3-pyrazolidone, 1-phenyl-4-hydroxymethyl-4-methyl-3-pyrazolidone, N-methyl-p-aminophenol and sulfate thereof, hydroquinone and sulfonate thereof, and so on.

Color and the black-and-white developers also contain sulfites such as sodium sulfite, potassium sulfite, sodium hydrogen sulfite, potassium hydrogen sulfite, sodium metasulfite, potassium metasulfite, etc., or adducts of carbonyl compounds and sulfites are usually contained as preservatives. The amount of these preservatives ranges from 0 to 5 g per liter of developer.

Various kinds of hydroxylamines are also present in the color and the black-and-white developers, as preservatives. Such hydroxylamines include unsubstituted and substituted hydroxylamines. Examples of substituted hydroxylamines include hydroxylamines whose nitrogen is bonded to lower alkyl group(s) in the place of hydrogen(s), preferably two alkyl groups containing, e.g., 1-3 carbon atoms, in the place of hydrogens, namely N,N-dialkyl substituted hydroxylamines. These N,N-dialkyl substituted hydroxylamines are often used in combination with alkanolamines such as triethanolamine. A content of hydroxylamines ranges from 0 to 5 g per liter of developer.

The color and the black-and-white developers generally have a pH of 9-12. Various kinds of buffers are used to maintain the developer at such a pH. Examples of buffers include carbonates, phosphates, borates, tetraborates, hydroxybenzoates, glycine salts, N,N-dimethylglycine salts, leucine salts, norleucine salts, guanine salts, 3,4-dihydroxyphenylalanine salts, alanine salts, aminobutyrates, 2-amino-2-methyl-1,3-propanediol salts, valine salts, proline salts, trishydroxyaminomethane salts, lysine salts and so on. Of these salts, carbonates, phosphates, tetraborates and hydroxybenzoates are particularly used over others, because their solubilities are high, they have excellent buffering ability in a high pH region beyond pH 9.0, they do not adversely affect photographic properties (e.g., cause no fog) when added to developers, and they are inexpensive. The amount of buffer added ranges generally from 0.1 to 1 mol per liter of developer.

Various kinds of chelating agents are further added to the developers as a precipitation preventing agent for calcium and magnesium, or in order to enhance the stability of the developers. Typical examples of such chelating agents include nitrilotriacetic acid, diethylenetriaminepentaacetic acid, nitrilo-N,N,N-trimethylenephosphonic acid, ethylenediamine-N,N,N',N'-tetramethylenephosphonic acid, 1,3-diamino-2-propanoltetraacetic acid, transcyclohexanediaminetetraacetic acid, 1,3-diaminopropanetetraacetic acid, 2-phosphonobutane-1,2,4-tricarboxylic acid, 1-hydroxyethylidene-1,1-diphosphonic acid, and so on. These chelating agents may be used in the form of a combination of two or more thereof.

The developers contain various kinds of development accelerators. Suitable examples of development accelerators include thioether compounds, p-phenylenediamine compounds, quaternary ammonium salts, p-aminophenols, amine compounds, polyalkylene oxides, 1-phenyl-3-pyrazolidones, hydrazines, meso-ionic compounds, thione compounds, imidazoles, and so on.

Many color developers for color papers contain alkylene glycols and benzyl alcohol in addition to the above-described color developing agent, sulfites, hydroxylamine salts, carbonates, hard water softeners and other additives. On the other hand, developers for color negative films, those for color positive films and some developers for color paper do not contain any of those alcohols.

Further, a developer may contain bromide ion in order to prevent fog generation. However, it is also possible to use a bromide ion-free developer for photographic materials containing silver chloride as their main silver halide. In addition, compounds capable of providing chloride ion, such as NaCl, KCl and the like, can be present as inorganic antifoggants. Also, the developers frequently contain organic antifoggants. Examples of organic antifoggants which may be present include adenines, benzimidazoles, benzotriazoles and tetrazoles. The amount of these antifoggants ranges from 0.010 g to 2 g per liter of developer. Antifoggants present may also be those which are eluted from photographic materials during processing and accumulate in the developer. In accordance with the method of this invention, as described above, even wastes which have a total halogen ion concentration, including a chloride ion concentration and a bromide ion concentration, of $1 \times 10^{-3}$ mol or more per liter of the mixture can be treated effectively. In particular, the present invention is effective in treating a waste mixture having a bromide ion concentration of at least $1 \times 10^{-3}$ mol per liter.

Moreover, developers may contain various kinds of surface active agents such as alkylphosphonic acids, arylphosphonic acids, aliphatic carboxylic acids, aromatic carboxylic acids, etc., if desired.

As described above, the silver-recovery system waste is the residue obtained after silver is recovered from exhausted fixing, bleaching and bleach-fixing solutions.

Fixation is carried out in black-and-white photographic processing, after development-processing. In color photographic processing, generally bleaching is further carried out between development and fixation, but bleaching and fixation may be carried out at the same time using a combined bleaching and fixing (blix) bath. A bleaching solution contains, as an oxidizing agent, a complex salt of Fe(III) or Co(III) and an organic acid, such as EDTA, diethylenetriaminepentaacetic acid, nitrilotriacetic acid, 1,3-diaminopropanetetraacetic acid, phosphonocarboxylic acid, etc.; persulfates; quinones; and so on. In some cases, the bleaching solution may further contain a rehalogenating agent such as an alkali metal bromide, ammonium bromide or the like, borates, carbonates and nitrates, if desired. The fixing solution and the bleach-fixing solution may contain thiosulfates (including sodium salt and ammonium salt), acetates, borates, ammonium or potassium alum, sulfites and so on.

Washing and/or stabilization is generally carried out after fixing or a combined bleaching and fixing step in the photographic processing of silver halide photographic materials. In the washing step, bacteria can propagate in a washing tank to produce suspended matter, and the resulting suspended matter sticks to photographic materials processed therein. As a means of avoiding the difficulty, a method of lowering calcium and magnesium ion concentrations, as disclosed in JP-A-61-131632, can be used. Further, bactericides such as isothiazolone compounds and thiabendazoles disclosed in JP-A-57-8542; chlorine-containing germicides such as sodium salt of chlorinated isocyanuric acid; and other germicides including benzotriazoles, as described in Hiroshi Horiguchi, *Bohkin Bohbai-Zai no Kagaku* ("Antibacterial and Moldproof Chemistry"), *Buseibutsu no Mekkin Sakkin Bohbai Gijutsu* ("Arts of Sterilizing and Pasteurizing Microbes, and Proofing against Molds"), compiled by Eisei Gijutsukai, and *Bohkin-Bohbaizai Jiten* ("Thesaurus of Antibacterial and Antifungal Agents"), compiled by The Society for Antibacterial and Antifungal Agents, Japan.

A suitable pH for the washing water in the processing of light-sensitive materials ranges from 4 to 9, preferably from 5 to 8. Also, light-sensitive materials can be processed directly with a stabilizer instead of undergoing the above-described washing processing. All of known methods as disclosed in JP-A-57-8543, JP-A-58-14834 and JP-A-60-220345 can be employed as a stabilization.

On the other hand, stabilization may be carried out subsequent to the foregoing washing step. As an example, a stabilizing bath containing formaldehyde and a surface active agent, which is used as the final bath of color photographic materials for photographic use, can be used. Various kinds of chelating agents and antimolds can be added to such a stabilizing bath.

The photographic processing waste is a mixture of wastes from the above-described various kinds of processing baths for color and black-and-white photographic materials.

The main components of the silver-recovery system waste to which the present treatment is applicable have appropriate concentration ranges. Specifically, the appropriate concentration of ammonium thiosulfate ranges from 20 to 150 g/l, that of sodium sulfite from 1 to 10 g/l, that of acetic acid from 0 to 50 g/l, and that of ammonium ethylenediaminetetraacetatoferrate(III) from 2 to 40 g/l. More specifically, a typical example is a silver-recovery system waste containing about 90 g/l of ammonium thiosulfate, about 5 g/l of sodium sulfite, about 15 g/l of acetic acid and about 7 g/l of ammonium ethylenediaminetetraacetatoferrate(III).

The main components of the development system waste treatable by the present method and their respective concentration ranges are as follows: hydroquinone ranges in concentration from 4 to 30 g/l, color developing agents from 1 to 15 g/l, benzyl alcohol from 0 to 5 g/l, hydroxylamines from 0 to 4 g/l, acetic acid from 0 to 4 g/l, and 5-sulfosalicylic acid from 0 to 20 g/l. More specifically, a typical development system waste contains about 11 g/l of hydroquinone, about 3 g/l of a color developing agent, about 2 g/l of benzyl alcohol, about 1 g/ of hydroxylamine, about 1 g/l of acetic acid and about 7 g/l of 5-sulfosalicylic acid.

The concentration ranges of the main components set forth above are merely representative, and the application of the present invention should not be construed as being limited to wastes having concentration ranges as set forth above.

Silver-containing wastes undergo the biological treatment of this invention after recovery of silver therefrom.

The recovery of silver can be performed using various methods, e.g., a method of depositing silver electrolytically, a method in which steel wool is added to a silver-containing waste to convert silver ion to silver by taking advantage of the difference in ionization potential between silver and iron and to deposit silver on the steel wool, a method in which a sodium sulfide solution is added to a silver-containing waste to precipitate silver ion from the waste in the form of silver sulfide, and so on.

It is desirable in this invention to conduct an electrolytic oxidation treatment after the bio-oxidation treatment. Performing the bio-oxidation treatment and the electrolytic oxidation treatment in this order has advantages in that: (1) since ingredients which are biodegradable are degraded effectively in the process of the microbial oxidation treatment, a reduction in COD can be achieved and the electrolytic oxidation process subsequent to the bio-oxidation can have a reduced treatment load resulting in reduction in electricity consumption; (2) even when the photographic processing waste contains lower sulfur compounds such as thiosulfate ion, sulfite ion, etc., oxidation of such lower sulfur compounds can proceed with conversion to sulfate ion in the bio-oxidation treatment process, and so poisonous gases such as hydrogen sulfide are not evolved during the electrolytic oxidation process subsequent to the bio-oxidation treatment; (3) even when the photographic processing waste contains halogen ions such as bromide ion, chloride ion, etc., the addition of an alkali (e.g., sodium hydroxide, potassium hydroxide, calcium hydroxide, sodium carbonate) to the waste during electrolytic oxidation and thereby shifting the pH of the waste to the alkaline region prevents the evolution of poisonous halogen gases such as bromine gas, chlorine gas, etc. during the electrolytic oxidation and, what is more, an effective reduction in COD is achieved; and (4) even when the photographic processing waste contains aromatic compounds such as developing agents, the waste which has already undergone bio-oxidation does not soil electrodes, and so effective electrolytic oxidation becomes feasible.

The addition of an alkali in the electrolytic oxidation treatment, can be in the form of a solid, aqueous solution or suspension in an appropriate amount all at once prior to the electrolytic oxidation treatment. Also, the alkali may be continuously fed during the electrolytic oxidation treatment based on the interrelationship of pH. The pH of the electrolytic oxidation system is preferably maintained at 7 or higher, especially 8 or higher, during the treatment.

The electrolytic oxidation treatment which can be used in this invention is not particularly restricted as to anodes used therein, provided that they are sufficiently noble to not wear away even when anodic oxidation is carried out continuously. However, anodes sufficiently noble to be difficultly oxidized include those formed by covering the surface of a titanium substrate with lead dioxide, platinum, platinum-iridium alloy, iridium dioxide or so on (such as Exeroad, products of Japan Carlit, Co., Ltd.), and these are preferred. High voltage can be applied to such anodes and so they can be used to electrolytically oxidize alcohols, aldehydes, carboxylic acids and so on with high efficiency. Specifically, a voltage of 2-10 V, preferably 2-8 V, can be applied to one pair of electrodes.

On the other hand, any cathode can be used in this invention so long as it has sufficient corrosion resistance to not be corroded during suspension of electrolysis and high ability to transmit electric current. However, a stainless steel plate (or rod) is optimum therefor. Of course, various kinds of carbon electrodes and various metal electrodes can also be used. The structure of electrodes suitable for the electrolytic oxidation in this invention can include anode-cathode pairs which alternate an arrangement of positive and negative plates with appropriate intervals, or a group of electrodes may have a sandwich type structure where one positive plate is sandwiched between two negative plates, or one negative plate is sandwiched between two positive plates. These electrodes may have any form, including linear, plate, net, cloth and globe forms. However, a larger surface area is preferred.

The electrolytic bath may be designed for either continuous or batch operation, provided that the wastes to be treated can stay for a time long enough for the reaction to be completed. The agitation inside the electrolytic bath can be carried out using any means so long as the electrolytic solution on the electrode surface can be moved to a satisfactory extent. For example, the electrodes may be rotated, a gas may evolve due to electrolysis, a gas may be bubbled into the bath, a revolving plate or rod may be installed in the bath, or the electrolytic solution may be moved with a pump or due to gravity.

Further, metal or metallic compounds may be added as electrolytic catalyst to the electrolytic bath.

The quantity of electricity applied to the bath is the product of electric current and time, and is controlled to 0.1 –1,000 times, preferably 0.5–100 times, the COD equivalent. The term COD equivalent as used herein is double the product of the quotient of COD value divided by atomic weight of oxygen and the Faraday constant.

In many cases, the treatment performed in accordance with the above-described process can be used to convert the waste mixture to a harmless solution to enable discharge into a sewer or a river. In a particular case where wastes of high concentrations are treated, the wastes can further be subjected to an adsorption treatment using active carbon to lower the pollution level upon discharge if necessary.

The evolution of poisonous gases and the soiling of the electrodes with a tarry material during electrolytic oxidation treatment can be inhibited by carrying out the biological treatment prior to the electrolytic oxidation. This is because the biological treatment can convert thiosulfate ion to sulfate ion through complete oxidation to prevent the evolution of hydrogen sulfide and can degrade aromatic compounds such as a developing agent to prevent polymerization thereof.

In addition, ingredients which have poor biodegradability, such as chelating agents including EDTA, can be effectively disposed of in the subsequent electrolytic oxidation treatment. This is also a striking effect of the present treatment, which cannot be obtained by carrying out the biological treatment after the electrolytic oxidation treatment.

Moreover, since silver-recovery system waste and development system waste are mixed and then subjected to the present treatment, a common treating bath can be used and the control system can be simplified. Therefore, the cost of equipment can be reduced, and the operation and the maintenance of the treating system is easy.

The present invention is now be illustrated in more detail by reference to the following examples. However, the invention should not be construed as being limited to these examples. Unless otherwise indicated herein, all parts, percents, ratios and the like are by weight.

EXAMPLE 1

Ten-Time Dilution Treatment of Mixture of Silver-Recovery System Waste and Development System Waste A silver-recovery system waste (obtained by mixing waste of the fixing solution used in the color photographic processing CN-16, waste of the mixture of the bleaching solution and the fixing solution used in the color photographic processing CN-16Q, waste of the blix solution used in the color photographic processing CP-20, waste of the blix solution used in the color photographic processing CP-23, waste of the black-and-white photographic fixing solution Fuji F, waste of black-and-white photographic fixing solution GR-Fl and water in a ratio of 4:1:3:2:7:3:2, and then by subjecting the mixture to a silver-recovery treatment) and a development system waste (obtained by mixing wastes of the developing solutions used in the color photographic processing CN-16, CN-16Q, CP-20 and CP-23, wastes of the black-and-white photographic developing solutions RD3 and GR-Dl, and water in a ratio of 4:1:3.2::7:3:2) were mixed in a ratio of 1:1 by volume. Because the inorganic salt concentration of the resulting mixture was 12%, that is to say, too high to be subjected to biological treatment, the mixture was diluted 10 times with city water. To the thus diluted waste, phosphorus was added in the form of dipotassium hydrogenphosphate in an amount corresponding to about 3% of the COD value of the diluted waste (about 4,700 ppm), and calcium and magnesium ions were further added in concentrations of 10 ppm and 2 ppm, respectively. The pH of the thus prepared waste was 8.5.

This waste was treated continuously with sulfur-oxidizing bacteria-containing activated sludge [MLSS (Mixed Liquor Suspended Solids): 4500 ppm]. In using the activated sludge for the present treatment, it was acclimated in advance over a period of one month by feeding continuously a 10-time diluted solution of silver-recovery system waste (COD: about 4,500 ppm) to the sludge and using HRT of 2 days. HRT of the waste for the treatment was controlled to 2 days.

Sulfuric acid produced therein was neutralized with a 10% aqueous solution of sodium hydroxide so that the pH of the liquid in the aeration tank was kept at a value higher than 6.6. The pH adjustment was carried out with a pH controller Model FC-10 (made by Tokyo Rika).

The results of this treatment are shown in Table 1. Additionally, the activated sludge used in this treatment continued to remain in a good condition for two months or longer.

All the underlined processing solutions cited above are products of Fuji Photo Film Co., Ltd.. They each contain the following amounts of compounds as their respective main components.

Silver-Recovery System

CN-16: 13 g/l of sodium sulfite, 120 g/l of ammonium thiosulfate, and 5 g/l of ammonium ethylenediaminetetraacetatoferrate(III).

CN-16Q: 12 g/l of sodium sulfite, 130 g/l of ammonium thiosulfate, and 100 g/l of ammonium ethylenediaminetetraacetatoferrate(III).

CP-20: 2 g/l of sodium sulfite, 48 g/l of ammonium thiosulfate, and 20 g/l of ammonium ethylenediaminetetraacetatoferrate(III).

CP-23: 3 g/l of sodium sulfite, 50 g/l of ammonium thiosulfate, and 25 g/l of ammonium ethylenediaminetetraacetatoferrate(III).

Fuji F: 6 g/l of sodium sulfite, and 100 g/l of ammonium thiosulfate.

GRFl: 7 g/l of sodium sulfite, and 135 g/l of ammonium thiosulfate.

Development System

CN-16 5 g/l of a developing agent, and 3 g/l of sodium sulfite.

CN-16Q: 7 g/l of a developing agent, and 4 g/l of sodium sulfite.

CP-20: 4 g/l of a developing agent, 1 g/l of sodium sulfite, and 11 g/l of benzyl alcohol.

CP-23: 5 g/l of a developing agent, 1.5 g/l of sodium sulfite, and 13 g/l of benzyl alcohol.

RD3: 22 g/l of sodium sulfite, and 12 g/l of hydroquinone.

GRD1: 32 g/l of sodium sulfite, and 9 g/l of hydroquinone.

EXAMPLE 2

Six-Time Dilution Treatment of Mixture of Silver-Recovery System Waste and Development System Waste A 1:1 by volume mixture of the same silver-recovery system waste and the same development system waste as used in Example 1 was diluted six times with water, and calcium and magnesium in the same concentrations as in Example 1 were added thereto. To the resulting solution, phosphorus was further added in the form of dipotassium hydrogenphosphate in an amount corresponding to 3% of the COD value of the solution (about 7,800 ppm). The thus prepared solution was subjected to a biological treatment with sulfur-oxidizing bacteria-containing activated sludge under the same condition as in Example 1. The results of this treatment are shown in Table 1 below.

Additionally, the activated sludge used in this treatment continued to remain in good condition for one month or longer.

EXAMPLE 3

Treatment in Which Amount of Phosphorus added Corresponded to 2% of COD Value

The same treatment as in Example 1 was carried out, except that the amount of phosphorus added was controlled to 2% of the COD value (about 4,700 ppm). The results obtained are shown in Table 1 below.

Additionally, the activated sludge used in this treatment continued to remain in good condition for two months or longer.

In the 10-time diluted solution of the 1:1 by volume mixture of the silver-recovery system waste and the development system waste, which was used in Example 1, the concentration of the silver-recovery system waste and that of the development system waste were 1/20 of their respective initial values. In Comparative Examples 1 and 2 described below, therefore, the silver-recovery system waste and the development system waste each were diluted 20 times, and subjected to the same biological treatment as in Example 1.

COMPARATIVE EXAMPLE 1

Treatment of Silver-Recovery System Waste Alone

The same silver-recovery system waste as described in Example 1 was diluted 20 times. Thereto, phosphorus, calcium ion and magnesium ion were added in the same proportion as in Example 1, respectively. Then, the resulting waste was treated biologically using the sulfur-oxidizing bacteria-containing activated sludge under the same condition as in Example 1. The results obtained are shown in Table 1 below. Additionally, the activated sludge used in this treatment continued to remain in a good condition for two months or longer.

COMPARATIVE EXAMPLE 2

Treatment of Development System Waste Alone

The same development system waste as described in Example 1 was diluted 20 times. Phosphorus, calcium ion and magnesium ion were added thereto in the same proportion as in Example 1, respectively. Then, the resulting waste was treated biologically using the sulfur-oxidizing bacteria-containing activated sludge under the same conditions as in Example 1. The results obtained are shown in Table 1 below. Additionally, the MLSS value of the activated sludge used in this treatment began to show a gradual decrease at the third week or so after the start of the treatment, and the activated sludge ceased to be in good condition in less than 2 months.

COMPARATIVE EXAMPLE 3

Modification of Example 1 in Which Amount of Phosphorus Added Corresponds to 1% of COD Value.

A 1:1 by volume mixture of the same silver-recovery system waste and the same development system waste as described in Example 1 was diluted ten times with water, and thereto were added calcium and magnesium in the same concentrations as in Example 1, respectively. Phosphorus was further added to the resulting solution, in the form of dipotassium hydrogenphosphate in an amount corresponding to 1% of the COD value of the solution (about 4,700 ppm). The thus prepared solution was subjected to the biological treatment with sulfur-oxidizing bacteria-containing activated sludge under the same conditions as in Example 1.

The results of this treatment are shown in Table 1 below.

Additionally, the activated sludge used in this treatment began to break up at the third week after the start of the treatment, and so a satisfactory treatment became impossible.

TABLE 1

|  | Example 1 | Example 2 | Example 3 | Comparative Example 1 | Comparative Example 2 | Comparative Example 3 |
|---|---|---|---|---|---|---|
| Original Waste | 10-Time dilution of waste mixture | 6-Time dilution of waste mixture | 10-Time dilution of waste mixture | 20-Time dilution of Ag-recovery system waste | 20-Time dilution of development system waste | 10-Time dilution of waste mixture |
| COD (ppm) of Original Waste | 4,700 | 7,800 | 4,700 | 2,300 | 2,400 | 4,700 |
| COD (ppm) of Treated Waste | 800 | 1,400 | 830 | 480 | 840* | 890* |
| Treatability (%) | 83 | 82 | 82 | 79 | 65** | 81** |
| Condition of Activated Sludge | Good | Good | Good | Good | Sludge broke up 2 months after | Sludge broke up 3 weeks after |
| Amount of Phosphorus Added | 3% of COD | 3% of COD | 2% of COD | 3% of COD | 3% of COD | 1% of COD |

*The minimum COD value of the treated waste was set forth. The COD value of the treated waste increased sharply after break up of the sludge.
**The treatability deteriorated with an increase in COD of the treated waste after break up of the sludge.

The original wastes used in Example 1 and Example 2 had the BOD values of 3,800 ppm and 6,200 ppm, respectively.

As can be seen from the results for Example 1 and Example 2 and the results shown in Table 1, the biological treatment of high concentration photographic processing wastes greater than 3,000 ppm in BOD value, which had previously been difficult to process, was achieved stably with high efficiency in accordance with the present invention.

Further, it is evident from the results in Table 1 that in accordance with the present invention, a premixed treatment of the silver-recovery system waste and the development system waste was possible and not only did the treatment of the development system waste become feasible because the activated sludge remained in a good condition but also an elevation of treatability was achieved. This is in contrast to the independent treatment of the development system waste as in Comparative Example 2.

Furthermore, it was necessary to add phosphorus in this invention in an amount corresponding to 2% or more of the COD value of the waste to be treated, as indicated from the comparative examples and Example 3. Additionally, when city or well water containing calcium and magnesium in proper amounts was used as a diluent, the treatment results were obtained which were almost equivalent to the case in which these ions were added without taking the trouble to add these ions. That is, the addition of calcium and magnesium ions can be omitted depending on the kind of diluent used.

EXAMPLE 4

Description of Waste Used

Various kinds of commercially available multilayer color negative films, including Fuji Color SUPER HG (abbreviated as SHG-)100, SHG-200, SHG-400, SHG-1600, REALA (which all are the products of Fuji Photo Film Co., Ltd.), Kodacolor GOLD (abbreviated as GOLD-)100, GOLD-200, GOLD-400, GOLD-1600, Ekta-25, Ekta-125, Ekta-1000 (which all are the products of Eastman Kodak Co.), Konica Color-GX (abbreviated as GX-)100, GX-200, GX-400, GX-3200, Konica Color-GXII (abbreviated as GXII-)100 and GX-100M (which are the products of Konica Corporation), which had been used for picture-taking, were processed together successively without any special grouping using a film processor for a mini laboratory, FP900AL (trade name, made by Fuji Photo Film Co., Ltd.) and a color negative processing agent CN-16Q (trade name, made by Fuji Photo Film Co., Ltd.). The overflow from the developing and the washing baths used in this processing was taken as color negative development system waste, and that from the bleaching and the fixing baths as color negative bleach-and-fix system waste. In addition, printing was carried out using color papers (Fuji Color Paper SUPER FA, trade name, produced by Fuji Photo Film Co., Ltd.) from color negative films, and the resulting color papers were processed using a processing agent for color paper CP-43FA (trade name, produced by Fuji Photo Film Co., Ltd.) and a printer processor PP1800B (trade name, made by Fuji Photo Film, Co., Ltd.). The overflow from the developing bath used therein was taken as color paper development system waste, and the overflow from the blix and the washing baths as color paper bleach-fix system waste.

The above color negative development system waste and the above color paper development system waste were mixed in a ratio of 1:1 by volume, and this mixture was taken as color development system waste, while a 1:1 by volume mixture of the above color negative bleach-fix system waste and the above color paper bleach-fix system waste was taken as color bleach-and-fix system waste.

Various kinds of commercial available black-and-white negative films, including Neopan SS, Neopan 400 PRESTO, Neopan 1600 SUPER PRESTO (which are all the products of Fuji Photo Film Co., Ltd.), which had already been used for picture-taking, were processed altogether without any special grouping using successively a developer Fuji Dol and a fixer Fuji Fix (products of Fuji Photo Film Co., Ltd.). Five liters of each of the wastes from these processing steps were collected. Then, the printing was carried out on commercial available black-and-white papers (Fuji Bro WP, products of Fuji Photo Film Co., Ltd.) from the above negatives, and the resulting papers were processed successively with a developer Korectol and a fixer Fuji Fix (products of Fuji Photo Film Co., Ltd.). Five liters of each of the wastes from these processing steps were collected. Further, medical X-ray films MI-SF and MI-SFII (products of Fuji Photo Film Co., Ltd.) were processed with a developer RD-3 and a fixer Fuji-F (products of Fuji Photo Film Co., Ltd.), and 10 liters of each of the wastes therefrom were collected. Furthermore, 10 liters of the wastes from the processing of graphic arts films using the developer and the fixer of System Fuji GRADEX Series, GR-Dl and GR-Fl (trade name, produced by Fuji Photo Film Co., Ltd.) were collected. These wastes were grouped into those from the development step and those from the fixing step, and mixed independently. The total volume of each waste group was 30 liters. The waste group from the developing step was named black-and-white development system waste, while that from the fixing step was named black-and-white fixing system waste.

The color development system waste and the black-and-white development system waste were mixed in a ratio of 1:1 by volume, and taken as a development system waste. On the other hand, the color bleach-and-fix system waste and the black-and-white fixing system waste were mixed in a ratio of 1:1 by volume, and subjected to a silver-recovery treatment. The resulting waste was taken as a silver-recovery system waste. These development system and silver-recovery system wastes were mixed in a ratio of 1:1 by volume, and subjected to the treatment of this invention.

The COD value of the thus prepared waste mixture was 45,000 ppm determined using the manganese method. This waste mixture contained as developing agents 0.084 mol/l of hydroquinone, 0.01 mol/l of N-ethyl-N-($\beta$-methanesulfonamidoethyl)-3-methyl-4-aminoaniline and 0.015 mol/l of 2-methyl-4-[N-ethyl-N-($\beta$-hydroxyethyl)amino]aniline, as lower sulfur compounds 0.31 mol/l of thiosulfate ion and 0.12 mol/l of sulfite ion, and as a chelating agent 0.9 millimole/l of EDTA. In addition, 0.047 mol/l of bromide ion and 0.004 mol/l of chloride ion were present. Thus, this waste mixture had an inorganic salt concentration of 12%.

The foregoing waste mixture was diluted 10 times by volume with city water. To the thus diluted waste, phosphorus was added in the form of dipotassium hydrogenphosphate in an amount corresponding to 3% of the COD value of the diluted waste (about 4,500 ppm), and calcium and magnesium ions were further added in concentrations of 10 ppm and 2 ppm respectively. This waste was treated continuously with sulfur-oxidizing bacteria-containing activated sludge (MLSS: 4500 ppm). HRT of the waste during the treatment was controlled to 2 days. Sulfuric acid produced therein was neutralized with a 10% aqueous solution of sodium hydroxide so that the pH of the liquid in the aeration tank was kept at a value higher than 6.6.

The above-described biological treatment was carried out continuously until it functioned in a steady condition [the foregoing procedures which had been performed till this condition was achieved were named collectively Treatment (a)], and the treated waste obtained hereinafter was designated simply treated waste. From the treated waste, the suspended matter was filtered out, and the resulting filtrate was subjected to an electrolytic oxidation treatment [Treatment (b)], wherein the filtrate was shared by five 2-liter electrolytic baths connected in series, each of which were equipped with a lead dioxide plate as anodes (Model LD 400, products of Japan Carlit Co., Ltd.) sandwiched between two stainless steel plates (SUS 316) as cathodes, and to which an electric current of 10 A was applied and the filtrate was stirred vigorously. In Treatment (b), 2 electric current-application times were used, and the thus treated wastes were designated Treated Waste 1 and Treated Waste 2, respectively. The results obtained are shown as those of Experiments No. 1 and No. 2 in Table 2 below. The pH of the electrolytic baths in these two cases were both about 1.9. As the result of the above-described treatments, the treated wastes became clear and had a low pollution load, that is, the COD value of below 330 ppm and the EDTA concentration of below 0.01 millimole/l. Additionally, in both cases, neither evolution of hydrogen sulfide gas nor soiling of the anode occurred. Moreover, by repeating the above-described procedures the treatment of wastes could be effected continuously with high reproducibility.

EXAMPLE 5

After the same Treatment (a) as in Example 4 was carried out, Treatment (b) was performed in the same manner as in Example 4, except that a pH controller was mounted in one of the electrolytic baths as used in Example 4 and an electric current of 10 A was applied to the baths with vigorous stirring while the pH inside the baths under the electrolytic oxidation treatment was kept at 8±0.1 by feeding a 10% aqueous solution of sodium hydroxide into the baths. In this Treatment (b), 2 electric current-application times were adopted, and the thus treated wastes were designated Treated Waste 3 and Treated Waste 4 respectively. The results obtained are shown as those of Experiments No. 3 and No. 4 in Table 2 below. Thus, similar to Example 4, the treated wastes became clear and had a low pollution load, that is, with a COD value of below 140 ppm and an EDTA concentration of below 0.01 millimole/l. As can be clearly seen from a comparison with the results of Experiments No. 1 and No. 2, the present invention was able to lower the COD value under the same electric current-application time. Additionally, in both cases, neither evolution of hydrogen sulfide gas nor soiling of the anode occurred. Moreover, halogen gases were not produced.

EXAMPLE 6

Treated Waste 2 obtained in Example 4 and Treated Waste 2 obtained in Example 5 were passed through a column packed with granular active, carbon TYPE SGL (produced by Toyo Chalgone Co.), independently. The resulting wastes had COD values of 50 ppm and 27 ppm, respectively. A satisfactory reduction in COD value was achieved.

COMPARATIVE EXAMPLE 4

The same Treatment (b) as in Example 4 was carried out without performing any Treatment (a). The data of the thus Treated Wastes 5 and 6 are shown as the results of Experiments No. 5 and No. 6 in Table 2 below. In comparison with the results obtained in Example 4, the reduction in COD under the same electric current-application time was not satisfactory and, what was worse, hydrogen sulfide gas was evolved. In addition, EDTA was not completely decomposed, and tar was generated soiling the electrodes seriously. Consequently, the tar adhered on the electrodes had to be removed to carry out the treatment repeatedly.

TABLE 2

| | Experiment No. | | | | | |
|---|---|---|---|---|---|---|
| | 1 | 2 | 3 | 4 | 5 | 6 |
| Treated Waste | Treated Waste 1 | Treated Waste 2 | Treated Waste 3 | Treated Waste 4 | Treated Waste 5 | Treated Waste 6 |
| Treatment (a) | Performed | Performed | Performed | Performed | Not Performed | Not Performed |
| COD (ppm) | 800 | 800 | 800 | 800 | 4,500 | 4,500 |
| EDTA (mmol/l) | 0.98 | 0.98 | 0.98 | 0.98 | 0.99 | 0.99 |
| Treatment (b) | | | | | | |
| Electric Current Application Time | 4 hrs. | 6 hrs. | 4 hrs. | 6 hrs. | 4 hrs. | 6 hrs. |
| COD (ppm) | 330 | 220 | 140 | 120 | 1,400 | 1,100 |
| EDTA (mmol/l) | <0.01 | <0.01 | <0.01 | <0.01 | 0.17 | 0.08 |
| Evolution of $H_2S$ gas | Absent | Absent | Absent | Absent | Present | Present |
| Evolution of $Br_2$ gas | Present | Present | Absent | Absent | Present | Present |
| Anode Soiling | Absent | Absent | Absent | Absent | Tar adhesion | Tar adhesion |
| Note | Invention | Invention | Invention | Invention | Comparison | Comparison |

COMPARATIVE EXAMPLE 5

To the Treated Waste 6 obtained under the electric current-application time for 6 hours in Comparative Example 4, phosphorus was added in the form of dipotassium hydrogenphosphate in an amount corresponding to 1% of the COD value of the waste (1,100 ppm), and calcium and magnesium ions were further added in concentrations of 10 ppm and 2 ppm respectively. The resulting waste was placed in an aeration tank, and the pH inside the tank was adjusted to 7 by the addition of a 10% aqueous solution of sodium hydroxide. This waste was treated continuously with sulfur-oxidizing bacteria-containing activated sludge (MLSS: 4500 ppm). HRT of the waste in the treatment was controlled to 2 days. In other words, the treatment of this invention were carried out in reverse order, that is, the bio-oxidation treatment was performed after the electrolytic oxidation treatment. The thus obtained Treated Waste 7 had a COD value of 550 ppm, and so the reduction in COD was not satisfactory in comparison with that achieved in Example 4 under the same electric current-application time. In addition, the EDTA concentration was 0.08 millimole/l, so the decomposition of EDTA was insufficient, as well.

In accordance with embodiments of this invention, it becomes feasible to treat biologically photographic processing wastes which contain reducible inorganic sulfur compounds and organic compounds such as developing agents in high concentrations. In particular, photographic processing wastes whose COD values are in the range of 3,000 to 8,000 ppm, that is, too high to be treated by conventional methods, can be converted to the treated wastes with low COD value by the present biological treatment. Although photographic processing wastes were difficult to treat biologically because of their high salt concentrations, the present treatment makes it feasible to perform a biological treatment in a stable manner and continuously over a long period of time without increasing the dilution of the wastes.

By further carrying out an electrolytic oxidation treatment after the bio-oxidation treatment of the mixture of a silver-recovery system waste and a development system waste, the treatment of not only biodegradable ingredients but also ingredients with poor biodegradability, such as chelating agents including EDTA, which are present in photographic processing wastes, can be achieved, efficiently and cheaply and in a steady manner without evolution of poisonous gases and generation of tar.

While the invention has been described in detail and with reference to specific embodiments thereof, it will be apparent to one skilled in the art that various changes and modifications can be made therein without departing from the spirit and scope thereof.

What is claimed is:

1. A method of treating photographic processing wastes, which comprises
   (1) mixing a silver-recovery system waste and a development system waste from photographic processing to produce a waste mixture,
   (2) adding to said waste mixture phosphorus, in the form of a compound selected from the group consisting of $KH_2PO_4$, $K_2HPO_4$, $NaH_2PO_4 \cdot 2H_2O$, and $Na_2HPO_4$, as a nutritive substrate in an amount corresponding to at least 2% based on the COD value of the waste mixture, and
   (3) subjecting the resulting waste mixture to a bio-oxidation treatment carried out by aeration using microflora containing sulfur-oxidizing bacteria selected from the group consisting of the Thiobacillus genus, the Thiotrix genus, and the Beggiatoa genus, and
   (4) subjecting the bio-oxidation treated waste mixture to an electrolytic oxidation treatment at a pH of 7 or higher.

2. The method as in claim 1, wherein said bio-oxidation treatment in step (3) is a treatment with activated sludge containing sulfur-oxidizing bacteria.

3. The method as in claim 1, wherein the pH of said microflora used for a bio-oxidation treatment in step (3) is 5.5 to 8.5.

4. The method as in claim 1, wherein said waste mixture in step (1) has a COD value of from 3,000 to 8,000 ppm.

5. The method as in claim 1, wherein said silver-recovery system waste comprises ammonium thiosulfate in an amount of from 20 to 150 g/l and sodium sulfite in an amount of from 1 to 10 g/l.

6. The method as in claim 1, wherein said development system waste comprises hydroquinone in an amount of from 4 to 30 g/l and a color developing agent in an amount of from 1 to 15 g/l.

7. The method as in claim 1, wherein said electrolytic oxidation treatment of step (4) is carried out in the presence of an alkali.

8. The method as in claim 7, wherein the alkali is selected from the group consisting of sodium hydroxide, potassium hydroxide, calcium hydroxide and sodium carbonate.

9. The method as in claim 1, wherein the anode used in said electrolytic oxidation treatment of step (4) is selected from those formed by covering the surface of a titanium substrate with lead dioxide, platinum, platinum-iridium alloy or iridium dioxide.

10. The method as in claim 1, wherein the electrolytic voltage for said electrolytic oxidation treatment of step (4 is 2 to 10 v.

11. The method as in claim 1, wherein the quantity of electricity is 0.1 to 1,000 times the COD equivalent.

12. A method as in claim 1, wherein the phosphorus as a nutritive substrate is added to said waste mixture in an amount corresponding to from 2% to 5% of the COD value of the waste mixture.

13. The method as in claim 1, wherein the pH of said microflora used for the bio-oxidation treatment in step (3) is from 5.8 to 7.5.

14. The method as in claim 1, wherein the pH of said microflora used for the bio-oxidation treatment in step (3) is from 6.5 to 7.0.

* * * * *